United States Patent [19]

Li

[11] 4,103,005
[45] Jul. 25, 1978

[54] NOVEL-ENKEPHALIN ANALOGS

[75] Inventor: Choh Hao Li, Berkeley, Calif.

[73] Assignee: Hoffmann-La Roche Inc., Nutley, N.J.

[21] Appl. No.: 843,778

[22] Filed: Oct. 20, 1977

[51] Int. Cl.$^2$ .................... A61K 37/00; C08L 37/00; C07C 103/52

[52] U.S. Cl. ........................ 424/177; 260/8; 260/112.5 R

[58] Field of Search ............ 260/8, 112.5 R; 424/177

[56] References Cited

PUBLICATIONS

Bajusz, et al., Febs. Letters 76, 91 (1977).
Felix, et al., Int. J. Pept. Proct. Res. 5, 201 (1973).
Rosamond, et al., J. Med. Chem. 19, 873 (1976).
Hambrook, et al., Nature (London), 262, 782 (1976).
Pert, et al., Science 194, 330 (1976).
Bajusz, et al., Acta Biochem. Biophys. Acad. Sci. Hung. II, 305 (1976).
Roemer, et al., Nature 268, 547 (1977).

*Primary Examiner*—Delbert R. Phillips
*Attorney, Agent, or Firm*—Samuel L. Welt; George M. Gould

[57] ABSTRACT

Two enkephalin analogs, [D-Met$^2$, Thz$^5$]-enkephalinamide and [D-Thr$^2$, Thz$^5$]-enkephalinamide have been found to be potent analgesic agents.

9 Claims, No Drawings

NOVEL-ENKEPHALIN ANALOGS

BACKGROUND OF THE INVENTION

The enkephalinamide compound [D-Met$^2$, Pro$^5$]-enkephalinamide has been reported to be a potent analgesic agent by Bajusz et al., FEBS Letters 76, 91 (1977).

It has been known in the art that proline can be replaced by thiazolidine-4-carboxylic acid (Thz) in biologically active peptides. See for example Felix et al., Int. J. Pept. Prot. Res. 5, 201 (1973) and Rosamond and Ferger, J. Med. Chem. 19, 873 (1976).

Further it is known that the 2-position in met-enkephalin appears to be sensitive to the nature of the side chain. Hambrook et al., Nature (London) 262, 782 (1976); Pert et al., Science 194, 330 (1976); and Bajusz et al.; Acta Biochim. Biophys. Acad. Sci., Hung. 11, 305 (1976).

Recently Roemer et al., Nature 268, 547 (1977) have reported on several met-enkephalin analogs, the most potent analgesic of the group being D-Ala$^2$, MePhe$^4$, Met-O$^5$-ol enkephalin which was indicated to be orally active.

DESCRIPTION OF THE INVENTION

The present invention relates to the novel enkephalin analogs [D-Met$^2$,Thz$^5$]-enkephalinamide and [D-Thr$^2$,Thz$^5$]-enkephalinamide. These two new enkephalin analogs were found to be potent analgesic agents.

The compounds of the present invention are readily prepared by solid phase procedures well known in the art such as for example as described by Merrifield, J. Am. Chem. Soc., 85, 2149 (1963). The resin support utilized in such procedures can be any conventional resin employed in solid phase synthesis such as a copolystyrenedivinylbenzene resin. The resin's terminal reactive site for coupling the first amino acid onto the resin can be halomethyl, such as bromo- or chloromethyl, or hydroxymethyl. If such resin forms are used, then the resulting peptide product obtained after cleavage of the resin contains a carboxy terminus carboxyl group which must then be converted into the desired amide form by methods known per se. Suitable procedures for this purpose include formation of a lower alkyl ester, such as the methyl ester, followed by ammonialysis or by treatment of the carboxyl peptide with ammonia in the presence of dicyclohexylcarbodiimide. Alternatively, the desired peptide amide can be obtained by ammonialysis of the peptide resin.

In preferred embodiments of the present invention the resin used is a commercially available copolystyrene-divinylbenzene resin in the benzhydrylamine or p-methoxybenzylamine form. Most preferred is the benzhydrylamine form. Cleavage of the peptide from this resin form by conventional procedures such as, for example, by treatment with HF in the presence of anisole, produces the amide function at the carboxy terminus directly.

The compounds of the present invention are useful as analgesic agents. Suitable dosage regimens for this purpose include a parenteral dosage of from 0.1 to 100 mg/kg, most preferably 1 to 10 mg/kg, which may be repeated as needed. The active compounds are most preferably formulated by passing an aqueous solution through a sterile filter to remove any bacterial contamination lyophilizing the subdivided filtrate in vials containing the desired amount of compound and then reconstituting the lyophilized solid with sterile isotonic saline or distilled water prior to administration.

The preparation and biological activity of the compounds of the invention is further illustrated by the following Example.

EXAMPLE

Materials and Methods

N-Boc-O-benzyl-D-threonine was prepared in the same way as reported by Mizoguchi, J. Org. Chem. 33, 903 (1968) for the L-isomer from D-threonine: mp 114°–116°, $[\alpha]_D^{24}$ −16.40 (c 2.25 methanol).

Anal. calcd. for $C_{16}H_{23}NO_5$ (309.36): C, 62.12; H, 7.49; N, 4.53. Found: C, 62.17; H, 7.42; N, 4.39.

The L-isomer has been reported to have mp 115°–116°, $[\alpha]_D$+15.8° (c 1.1, methanol).

Synthesis and characterization of peptides

Benzhydrylamine resin (1.505 g, 0.51 mmole/N/g, Beckman) was treated for 20 min with Boc-L-thiazolidine-4-carboxylic acid (4.87 mmole) that had been converted to the symmetrical anhydride by dicyclohexylcarbodiimide (2.25 mmole). After removal of the Boc group the Gisin amine test [Anal. Chim. Acta 58, 248 (1972)] was used by a procedure in which excess picric acid is washed out with 95% ethanol-$CH_2Cl_2$ (1:9, v/v). No amine was detected which suggested the imino group of the Thz residue is not basic enough to hold picric acid in the presence of 95% ethanol. Synthesis was continued by schedules described previsouly by Yamashiro and Li, Proc. Natl. Acad. Sci. USA 71, 4945 (1974). Boc-D-Met-OH, Boc(Bzl)-D-Thr-OH, and Boc(Z)Tyr-OH were used. After removal of the Boc group of Phe, amine determination showed 0.23 mmole/g. After incorporation of Gly, the resin was divided in half for synthesis of the two analogs. The final yield of the protected pentapeptide resins were 0.86 g each. The last Boc group was removed with trifluoroacetic acid using the procedure of Noble et al, J. Am. Chem. Soc. 98, 2324 (1976).

Each peptide resin was treated in liquid HF (15 ml) in the presence of anisole (2 ml) for 65 min at 0°. The resulting products were isolated by gel filtration on Sephadex G-10 in 0.5 N acetic acid. Purification was effected by partition chromatography in a 1.91 × 28 column of Sephadex G-25 in 1-butanol/3.5% acetic acid-1.5% pyridine (1:1) to yield H-Tyr-D-Met-Gly-Phe-Thz-NH$_2$ (I), R$_f$ 0.50, 23.5 mg and H-Tyr-D-Thr-Gly-Phe-Thz-NH$_2$ (II), R$_f$ 0.31, 21.0 mg. Each was homogeneous on thin-layer chromatography (ninhydrin and Cl$_2$-tolidine detection) in 1-butanol/pyridine/acetic acid/water (30:20:6:24) with R$_f$ 0.77 (I) and R$_f$ 0.75 (II) and in 1-butanol/acetic acid/water (4:1:5) with R$_f$ 0.55 (I) and R$_f$ 0.45 (II). Each was homogeneous on paper electrophoresis (Whatman 3 MM, 400 V, 6 hr) at pH 6.7 with R$_f$ 0.40 (I) and R$_f$ 0.38 (II) and at pH 3.7 with R$_f$ 0.45 (I) and R$_f$ 0.45 (II), all relative to Lys (ninhydrin detection). Amino acid analyses of 24 hr hydrolysates in 6 N HCl gave for I; Thz, 0.82; Gly, 0.99; Met, 104; Tyr, 1.01; Phe, 1.00; and for II: Thz+Thr, 1.7; Gly, 0.96; Tyr, 0.99; Phe, 1.00. Since Tyr values in Thz-containing peptides are low, they were obtained from analyses of 24-hr hydrolysates in 4 N methanesulfonic acid relative to Phe. Since Thz and Thr appeared at the same position on the analyzer, their sum in II was estimated from their known integration constants both at 570 nm and at 440 nm. As reported previously Thz is partly destroyed in hydrolysis.

In both syntheses, a significant by-product was isolated by partition chromatography amounting to one-half that of the major product; $R_f$ 0.45 in the synthesis of I and $R_f$ 0.060 in that of II. In the by-product of I, Phe was missing which indicates that the low basicity of the imino group of Thz resulted in incomplete incorporation of Phe.

For analgesic assay, male ICR mice weighing 25–30 g were used in all the experiments. The enkephalin analogs dissolved in saline were administered either centrally according to the method described by Haley and McCormick, Br. J. Pharmacol, 12, 12 (1957) or intravenously via the tail vein. The injection volume is 5 μl for central injection and 10 μl per gram body weight for intravenous injection. Naloxone HCl (3 mg/kg) was injected subcutaneously 5 min before the administration of enkephalin analogs. Analgesic activity was assayed by the tail-flick method of D'Amour and Smith, J. Pharmacol, Exp. Ther. 72, 74 (1941).

The percent of analgesia was calculated as $[(T_1-T_0)/(T_2-T_0)] \times 100$, where a control latency ($T_0$) was obtained from the mean of two latencies determined before drug injection; the test latencies ($T_1$) were determined at various times after injection for each animal; the cutoff time ($T_2$) for the tail-flick was 7 seconds. The median analgesic dose ($AD_{50}$) and 95% confidence limits were calculated according to the method of Litchfield and Wilcoxon, J. Pharacol. Exp. Ther. 96, 99 (1949). The locomotor activity to the mice was measured with an electronic Fe 40 motility meter (Motron Produkter, Stockholm, Sweden). The detail of the experimental method has been described by Tseng et al., Nature (London) 263, 239 (1976).

Results and Discussion

[D-Met², Thz⁵]-enkephalinamide (I) and [D-Thr², Thz5]-enkephalinamide (II) have been synthesized by the solid-phase method by a route designed to preserve the integrity of the Thz residue. The peptides were obtained in a high state of purity by partition chromatography, paper electrophoresis, and amino acid analysis. It was noted in the synthesis that the imino group of the Thz residue showed low basicity and low reactivity in the coupling step. The latter observation was confirmed in the synthesis of I by the isolation of the deletion peptide H-Tyr-D-Met-Gly-Thz-NH₂ during partition chromatography.

[D-Met²,Thz⁵]-enkephalinamide and [D-Thr²,Thz⁵]-enkephalinamide in doses of 0.17 to 0.85 μg and 0.011 to 0.085 μg respectively applied centrally induced a dose-related increase in intensity and duration of the tail-flick inhibition. The inhibition of the tail-flick response was mediated by opiate-like action as evidenced by the finding that it was blocked by the pretreatment of naloxone. As summarized in Table 1, the $AD_{50}$ of [D-Met³,Thz⁵]-enkephalinamide was 3.5 times higher than [D-Thr²,Thz⁵]-enkephalinamide. On molar basis, they are 7.7 and 27.1 times respectively more potent than morphine.

Table 1

Median Antinociceptive Doses ($AD_{50}$) of Morphine Sulfate and Opoild Peptides after Intravenous and Intracerebroventricular Injections in Mice

| Compound | Intravenous $AD_{50}$ᵃ μmole/kg | Potency ratio | Intracerebroventricular $AD_{50}$ᵃ nmole/mouse | Potency ratio |
|---|---|---|---|---|
| Morphine sulfate | 11.4ᵇ | 1 | 1.11ᶜ | 1 |
| β-Endorphin | 2.7ᵇ | 4.2 | 0.032ᶜ | 34.7 |
| D-Ala²,D-Leu⁵-Enkephalin | ≃30ᶜ | ≃0.4 | 0.035ᶜ | 31.7 |
| Met-enkephalin | >60 | <0.19 | >174 | <0.006 |
| D-Met²,Thz⁵-Enkephalinamide | 2.71 (1.75–4.19) | 4.2 | 0.145 (0.070–0.305) | 7.7 |
| D-Thr²,Thz⁵-Enkephalinamide | 2.40 (1.60–3.62) | 4.8 | 0.04 (0.026–0.063) | 27.1 |

In addition to the inhibition of tail-flick response, the mice exhibited strong Straub tail and increased locomotor activity. Thus, the behavior responses induced by these two pentapeptides are similar to morphine and [D-Ala²,Leu⁵]-enkephalin and were different from that produced by β-endorphin which has previously been shown to stimulate locomotor activity weakly or not at all.

[D-Met²,Thz⁵]-enkephalinamide and [D-Thr²,Thz⁵]-enkephalinamide in doses of 1.1 to 8.5 mg/kg injected intravenously were also active in inhibiting the tail-flick response. The duration and intensity of analgesia were dose-related. The duration of analgesia produced by [D-Thr²,Thz⁵]-enkephalinamide appeared to be longer than that produced by [D-Met²,Thz⁵]-enkephalinamide. [D-Thr², Thz⁵]-enkephalinamide is 3.5 times more potent than [D-Met², Thz⁵]-enkephalinamide when applied centrally, but the two are equipotent and 4.2–4.8 times more potent than morphine by intravenous injection (see Table 1).

I claim:

1. A [Thz⁵]-analog of enkephalinamide selected from [D-Met²,Thz⁵]-enkephalinamide and [D-Thr²,Thz⁵]-enkephalinamide.

2. The compund of claim 1 which is H-Tyr-D-Met-Gly-Phe-Thz-NH₂.

3. The compound of claim 1 which is H-Tyr-D-Thr-Gly-Phe-Thz-NH₂.

4. A compound of the formula

Boc-Tyr(Z)-D-Met-Gly-Phe-Thz-A where A is selected from benzhydrylamine or p-methoxybenzylamine copolystyrene-divinylbenzene resin and Z is benzyloxycarbonyl.

5. A compound of the formula

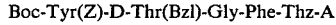

Boc-Tyr(Z)-D-Thr(Bzl)-Gly-Phe-Thz-A wherein A is selected from benzhydrylamine or p-methoxybenzylamine copolystyrene-divinylbenzene resin, Bzl is benzyl and Z is benzyloxycarbonyl.

6. A compound of the formula

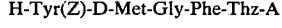

H-Tyr(Z)-D-Met-Gly-Phe-Thz-A wherein A is selected from benzhydrylamine or p-methoxybenzylamine copolystyrene-divinylbenzene resin, and Z is benzyloxycarbonyl.

7. A compound of the formula

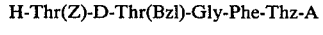

H-Thr(Z)-D-Thr(Bzl)-Gly-Phe-Thz-A wherein A is selected from benzhydrylamine or p-methoxybenzylamine copolystyrene-divinylbenzene resin, Bzl is benzyl and Z is benzyloxycarbonyl.

8. A method for producing an analgesic effect in a subject which method consists of administering to said subject an effective analgesic producing dose of a compound of claim 1.

9. The method of claim 6 wherein said effective dose is in the range of from 0.1 to 100 mg/kg administered parenterally.